US006979702B1

(12) United States Patent
Ma et al.

(10) Patent No.: US 6,979,702 B1
(45) Date of Patent: Dec. 27, 2005

(54) IONOMER COMPOSITE COMPOSITIONS (75) Inventors: Peter X. Ma, Ann Arbor, MI (US); Anne E. Huber, Novi, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/936,692

(22) PCT Filed: Mar. 16, 2000

(86) PCT No.: PCT/US00/06974

§ 371 (c)(1),
(2), (4) Date: Sep. 17, 2001

(87) PCT Pub. No.: WO00/55253

PCT Pub. Date: Sep. 21, 2000

Related U.S. Application Data

(60) Provisional application No. 60/124,819, filed on Mar. 17, 1999.

(51) Int. Cl.$^7$ .............................................. A61K 6/08
(52) U.S. Cl. ...................... 523/116; 523/115; 523/118; 433/228.1
(58) Field of Search ............................... 523/115–118; 433/228.1

(56) References Cited

U.S. PATENT DOCUMENTS

| 4,089,830 | A |   | 5/1978 | Tezuka et al. ............... 524/116 |
| 4,186,495 | A |   | 2/1980 | Remberg et al. ................ 34/92 |
| 4,527,979 | A |   | 7/1985 | McLean et al. ................ 106/35 |
| 4,569,954 | A | * | 2/1986 | Wilson et al. ............... 523/116 |
| 4,758,612 | A |   | 7/1988 | Wilson et al. .................. 524/5 |
| 4,772,325 | A |   | 9/1988 | Kwan et al. .................... 106/35 |
| 4,872,936 | A |   | 10/1989 | Engelbrecht ............ 156/307.3 |
| 5,051,453 | A |   | 9/1991 | Okabayashi et al. ........ 523/116 |
| 5,154,762 | A |   | 10/1992 | Mitra et al. .................. 523/116 |
| 5,367,002 | A |   | 11/1994 | Huang et al. |
| 5,520,725 | A | * | 5/1996 | Kato et al. ..................... 106/35 |
| 5,554,669 | A | * | 9/1996 | Nakabayashi et al. ....... 523/118 |
| 5,861,445 | A |   | 1/1999 | Xu et al. ..................... 523/116 |

FOREIGN PATENT DOCUMENTS

| EP | 323 120 A2 | 7/1989 |  |
| GB | 1507981 | 4/1978 | ............ C08K 3/34 |
| GB | 2 028 855 A | 8/1979 |  |
| WO | PCT/US00/06974 | 6/2000 |  |

OTHER PUBLICATIONS

Austenal Laboratories, Inc. v.Nobilium process Co. Jun. 5, 1957.*
0Petrolite Co. v. Watson Mar. 14, 1957.*
Forsten, L. and I. K. Paunio, *Fluoride release by silicate cements and composite resins*, Scandinavian Journal of Dental Research, 1972, vol. 80: pp. 515-519.

Corbin, S. B. and W. G. Kohn, *The benefits and risks of dental amalgam: Current finds reviewd*, JADA, Apr. 1994, vol. 125, pp: 381-388.
Bayne et al., *Update on dental composite restorations*, JADA, Jun. 1994, vol. 125, pp: 687-701.
Wilson, A. D. and B. E. Kent, *The Glass-Ionomer Cement, a New Translucent Dental Filling Material*, J. Appl. Chem. Biotechnol., Nov. 1971, vol. 21: p. 313.
Wilson, A. D. and B. E. Kent, *A New Translucent Cement for Denistry*, Br. Dent. J., Feb. 15, 1972, vol. 132: pp. 133-135.
McLean, J. W., *Cermet cements*, JADA, Jan. 1990, vol. 120: pp. 43-47.
Prosser, H. J., D. R. Powis and A. D. Wilson, *Glass-ionomer Cements of Improved Flexural Strength*, J. Dent. Res., Feb. 1986, vol. 65, No. 2: pp. 146-148.
Poolthong, S., T. Mori and M. V. Swain, *A Comparison of the Mechanical Properties of Three Glass-Ionomer Cements*, Dent. Mater. J., 1994, vol. 13, No. 2: pp. 220-227.
Hickel, R., *Glass Ionomers, Cermets, Hybrid-Ionomers and Componers- (Long-Term) Clinical Evaluation*, Acad. Dent. Mater. Trans., 1996, vol. 9: pp. 105-129.
Wilson, A. D. and J. W. McLean, *Glass Ionomer Cement*, Quintessence Publ. Co., 1988, Chapters 1-2: pp. 13-42.
Blackwell, G. and R. Kase, *Technical Characteristics of Light Curing Glass-ionomers and Compomers*, Acad. Dent. Mater. Trans., 1996, vol. 9: pp. 77-88.
Ma, X., J. A. Sauer, M. Hara, *Poly (methyl methacrylate) Based Ionomers. 1. Dynamic Mechanical Properties and Morphology*, Macromolecules, 1995, vol. 28, No. 11: pp. 3953-3962.
Kent, B., B. Lewis and A. D. Wilson, *Glass Ionomer Cement Formulations: 1. The Preparation of Novel Fluoroaluminocilicate Glasses High in Fluorine*, Journal of Dental Research, 1979, vol. 58, No. 6: pp. 1607-1619.
Wilson, A.D. et al., *Aluminosilicate Glasses for Polyelectrolyte Cements*, Ind. Eng. Chem. Prod. Res. Dev., 1980, vol. 19: pp. 263-270.

(Continued)

Primary Examiner—Peter Szekely
(74) Attorney, Agent, or Firm—Dierker & Associates, P.C.

(57) ABSTRACT

An ionomer composite composition having improved and unique physical properties, includes a glass material containing at least one of divalent cations and multivalent cations; and at least one copolymer. The copolymer comprises: at least one hydrophilic monomer containing acid functional groups adapted to react with the at least one of divalent cations and multivalent cations to form ionic crosslinks among polymer chains, the hydrophilic monomer present in an amount sufficient to impart a desired degree of aqueous solubility to the copolymer, and at least one hydrophobic monomer present in an amount sufficient to impart a desired degree of structural stability to the composite composition when exposed to an aqueous environment.

29 Claims, 6 Drawing Sheets

OTHER PUBLICATIONS de Araujo, F.B. et al., *Fluoride Release from Fluoride-containing Materials*, Operative Denistry, 1996, vol. 21: pp. 185-190.

Forsten, L., *Fluoride release and uptake by glass-ionomers and related materials and its clinical effect* Biomaterials, 1998, vol. 19: pp. 503-508.

Verbeeck, R. M. H., et al., *Fluoride release process of (resin-modified) glass-ionomer cements versus (polyacid-modified) composite resins*, Biomaterials, 1998, vol. 19: pp. 509-519.

Cross, M. et al, *The Relationship Between Filler Loading and Particle Size Distribution in Composite Resin Technology*, Journal of Dental Research, Jul. 1983, vol. 62, No. 7: pp. 850-852.

Söderholm, K.-J., *Relationship between commpressive yield strength and filler fractions of PMMA composites*, Acta Odontol. Scand., 1982, vol. 40: pp. 145-150.

Krause, W. R, *Mechanical properties of BIS-GMA resin short glass fiber composites*, Journal of Biomedical Materials Research, 1989, vol. 23: pp. 1195-1211.

* cited by examiner

IONOMER COMPOSITE COMPOSITIONS

CROSS REFERENCE TO RELATED APPLICATIONS

This application claims the benefit of U.S. Provisional Application Ser. No. 60/124,819, filed Mar. 17, 1999.

STATEMENT REGARDING FEDERALLY SPONSORED RESEARCH OR DEVELOPMENT

This invention was made in the course of research partially supported by a grant from the National Institute of Health/National Institute of Dental Research (NIH/NIDR) (Grant No. 2T3DE07057). The U.S. government has certain rights in the invention.

BACKGROUND OF THE INVENTION

The present invention relates generally to ionomer composite compositions, and more specifically to such compositions useful for many dental applications, ranging from direct restorative materials to fabrication of preformed structure for dental and osseous tissue repair applications.

It has been established that fluoride ions in the oral environment are beneficial to the reduction of recurrent caries, and formation of new caries. It is not currently known why fluoride ions contribute to a decrease in dental caries; theories include its effect on the bacteria, the formation of fluorapatite, and an increase in resistance to caries of both enamel and dentin. The glass filler used in composites and glass ionomers contains sufficient fluoride to see a reduction in caries in filled and surrounding teeth. In addition, the materials can be "recharged" through fluoride toothpaste and optical fluoride treatments.

It has been shown that dental silicate cements containing fluoride are therapeutic in preventing secondary caries and reducing plaque formation. Acrylic denture base material, restorative materials and adhesives have been shown to be sites of bacterial and plaque accumulation, which can be a precursor of irritation to soft tissues and caries attack on remaining natural dentition. The release of fluoride ion from these dental restorative materials generally occurs either by surface release, or by dissolution of the fluorine-containing additives or the dental restorative material itself with consequent migration of fluoride ions into the underlying tooth structure.

Various fluorine-containing additives that have been tried in dental restorations consist of inorganic fluoride salts, organic bases such as amine hydrofluoride, fluorocarbons and fluoride-containing ion-exchange resins. These attempts to find suitable fluorine-containing additives which are both dispersed in dental restorative material and capable of reducing tooth caries through controlled long-term fluoride release have failed. Silicate cements have demonstrated cariostatic release of fluoride. However, the strictly rapid surface release of fluoride from the cement, the dissolution of the cement in oral fluids, and the low tensile strengths of the cements are major disadvantages. Alternatively, the fluoride incorporated into insoluble resin materials has been considered to be virtually incapable of leaking out, and thus to be ineffective as a cariostatic agent Studies by Forsten and Paunio (*Scandinavian Journal of Dental Research* (1972) 80: 515–519) comparing fluoride release by silicate cements and composite resins have shown that the overall release of fluoride from the two materials was comparable; however, the manner in which the fluoride was released from the composite was not controlled. It was found difficult to obtain controlled, effective cariostatic and plaque-reducing fluoride release from virtually insoluble materials such as acrylic denture base materials, adhesives and composite resins, and the like.

U.S. Pat. No. 4,772,325 issued to Kwan et al. discloses a controlled, slow fluoride releasing additive comprising a Lewis base and a fluoride-containing Lewis acid which is therapeutic in preventing secondary caries and reducing plaque formation. This additive is incorporated into polymeric dental restorative material and is capable of migrating from the interior to the surface of the material without dissolution thereof and with consequent release of fluoride. However, this composition is merely an additive to existing dental restorative materials. Further, it does not increase desirable mechanical properties of the dental restorative material in which it is incorporated; nor does it improve adhesion between polymers.

Current dental composite resins comprise one end of a continuous spectrum of multi-phase dental materials, with glass ionomers at the other end. Hybrid materials such as resin-modified glass ionomers and compomers lie somewhere between. Whereas both composite resins and glass ionomers have been known and used for a relatively long period of time, the hybrid materials such as the resin-modified glass ionomers and compomers are relatively new.

Ceramic filler reinforced polymeric composites are widely used in the area of dental restorative materials. A typical dental composite is composed of a mixture of silicate glass or quartz particles with an acrylic monomer that is polymerized to form a hardened composite material. In current dental composites, the fillers are mostly glasses, occasionally glass-ceramics and quartz (a crystalline form of silica), particulate polymers and glass-polymer composite particulates. Strategies such as the development of smaller filler particles such as microfiller and nanofiller particles; the improvement of glass compositions; and the increase of filler volume fraction through the use of hybrid and heterogeneous filler systems have each been attempted in order to improve dental composites.

There is an increasing need to extend the use of polymeric composites to stress bearing posterior applications due to concerns about the release of mercury from dental amalgam. However, the relatively low toughness, strength, wear resistance and durability of current dental composites have limited their use. It is generally agreed that current polymeric composites cannot be routinely substituted for dental amalgam and achieve the same clinical results. In the posterior dentition, in situations where occlusal stresses are concentrated, the current composites are inappropriate choices (Corbin and Kohn, 1994, *JADA* 125: 381–388). The current polymer composites are not recommended for large posterior restorations because of the potential for excessive wear, microleakage or fracture (Bayne et al., 1994, *JADA* 125: 687–701). Composite restorations, in low stress-bearing applications not involving cusps, have average lifetimes of less than 10 years. In comparison, dental amalgam restorations, in high stress-bearing posterior applications with cusp replacement, have lifetimes of 15 years (Corbin and Kohn, 1994).

Many changes have occurred in recent years concerning dental restorative materials. Among these changes is the use of fluoride-releasing glass ionomer materials. Glass ionomer materials are based on the acid-base reaction of an aqueous solution of a polycarboxylic acid with an ion leachable, fluoride-containing glass (Wilson and Kent, 1971, *J. Appl. Chem. Biotechnol.* 21: 313; Wilson and Kent, 1972, *Br.*

Dent. J. 132: 133). Glass ionomers are noted for their inherent adhesiveness to teeth and their ability to release fluoride to adjacent tooth structure in a sustained fashion to combat secondary caries.

However, it is generally accepted that glass ionomers possess inferior mechanical properties, including extreme brittleness and low strength (e.g., flexural strength of 10–20 MPa--McLean, 1990, *J. Am. Dent. Assoc.* 120: 43). This mechanical inferiority has severely limited their use. The reinforcement of glass ionomers by disperse phase corundum (Prosser et al., 1986, *J. Dent. Res.* 65: 146), alumina fibers and other fibers (Sced and Wilson, Br. Pat. Application GB 2,028,855A, 1978), and metal powders (McLean and Gasser, U.S. Pat. No. 4,527,979, 1985) resulted in only incremental improvement in mechanical properties. Flexural strength values of reinforced glass ionomers have rarely exceeded 50 MPa (Wilson and McLean, *Glass-Ionomer Cement,* 1988; McLean, *J. Am. Dent. Assoc.,* 1990, 120: 43).

Resin-modified glass ionomers (Mitra, EP Application 323,120, 1988; U.S. Pat. No. 5,154,762, 1992), where compatible resins (e.g., 2-hydroxyethyl methacrylate, or HEMA) are used with the polyacids, are only slightly stronger than glass ionomers (e.g., flexural strength of 60 MPa—Poolthong et al., 1994, *Dent. Mater, J.* 13: 220; Hickel, 1996, *Acad. Dent. Mater. Trans.* 9: 105). It has been generally accepted that the most intractable problem is likely to be lack of strength and toughness (Wilson, A. D. and J. W. McLean, *Glass Ionomer Cement,* Quintessence Publ. Co. (1988)). For a further discussion of glass ionomers as used in the dental market for direct restorative materials, eg. as cure-in-mouth cements, see, for example, Wilson and McLean, (1988); Katsuyama, S., T. Ishikawa, et al., Eds., *Glass Ionomer Dental Cement—The Materials and Their Clinical Use,* Ishiyaka EuroAmercia Inc. (1993); and O'Brien, W., *Dental Materials and Their Selection,* Chicago, Quintessence Publ. Co. (1997).

Compomers have been developed recently. See, for example, U.S. Pat. No. 4,816,495 issued to Blackwell et al.; U.S. Pat. No. 5,367,002 issued to Huang et al.; and Blackwell et al., *Acad. Dent. Mater. Trans.,* 1996, 9: 77. Compomers are basically hybrid, glass ionomer-composites modified in their resin phase by a carboxylic acid monomer and in their filler phase by the inclusion of an acid-reactive, ion-leachable glass. The name compomer is derived by combining the two words composite and ionomer, and is intended to suggest a combination of composite and glass-ionomer technology. The liquid part of a compomer is a mixture of a dental resin monomer (such as UDMA, a urethane dimethacrylate) and a carboxylic acid monomer (e.g., TCB, the reaction product of butane tetracarboxylic acid with HEMA), with the resin being the major phase and TCB the minor phase. The filler part of a compomer is a mixture of dental silicate glass and reactive fluorosilicate glass particles, with the reactive glass being the minor phase.

In contrast to glass ionomers, compomers do not generally contain significant amounts of water. The sole initial curing reaction is radical induced polymerization of the acrylic resin monomer matrix. An acid-base reaction takes place between TCB and the ion leachable fluorosilicate glass only after water infuses the cured composite via exposure to oral fluids, which also causes the filling to release fluoride ions. Flexural strength values of 90–125 MPa have been reported for compomers (Hickel, 1996, *Acad. Dent. Mater. Trans.* 9: 105). However, these strength values are still inferior to those of current dental amalgam (100–150 MPa) and composite resins (100–145 MPa) (Hickel, 1996). Therefore, compomers are currently not recommended for use in large, stress-bearing posterior applications.

It has been generally recognized that glasses and glass-ceramics are among the weakest and most brittle materials to use as reinforcement fillers. Glass filler particles are sensitive to surface flaws produced during mixing, handling and wear. A crack in the resin matrix can easily cut through the reinforcing glass particles.

U.S. Pat. No. 5,861,445 issued to Xu et al. further defined geometrical shapes of the filler particles as cause for failure. The previously known glass fillers were either spherical or of irregular shapes, with length-to-diameter ratio only slightly larger than one. Xu et al., disclosed that this had at least two major short-comings. First, rounded filler particles at occlusal surfaces are susceptible to facile dislodgement from the resin matrix during wear with foods bolus, resulting in high wear rates. Second, if a crack is initiated in the composite, it can easily propagate around the filler particles, hence causing the reinforcing effect of the filler particles to be lost.

As an answer to those shortcomings, Xu et al. proposed the use of ceramic filler particles and whiskers and/or chopped fibers to reinforce polymeric dental composites so that there are substantially improved mechanical properties and enhanced clinical longevity compared to conventional (or currently used) materials. The elongated whiskers and chopped fibers were said to have high length-to-diameter ratio values to effectively bridge and resist micro-cracks. In addition, it was asserted that the whiskers were less likely to be dislodged out of the matrix during wear.

In the area of conventional preformed structure for dental and osseous tissue repair applications, there are several shortcomings inherent therein. For example, current plastic teeth offer low abrasion resistance, low crazing resistance, and low heat-distortion temperatures when compared to porcelain teeth. See, for example, Craig, R., Ed., *Restorative Dental Materials,* St. Louis, Mosby (1997). If these problems could be overcome, plastic denture teeth are already superior to porcelain teeth in toughness, natural feel, and ease of grinding and polishing (Craig 1997).

Thus, it is an object of the present invention to provide an ionomeric composite composition for dental application(s) which advantageously improves the wear properties of the composition in the dental application. It is a further object of the present invention to provide such a composition having a highly crosslinked structure, thereby advantageously improving the strength and crazing resistance of the composition in the dental application. Still further, it is an object of the present invention to provide such a composition which utilizes the unique properties of glass ionomers by advantageously adapting them for use in preformed denture teeth and other preformed structure. It is yet another object of the present invention to provide an ionomeric composite advantageously utilizing a copolymer as one component thereof. Yet still further, it is an object of the present invention to provide such a composition which may advantageously be varied to suit a wide variety of dental applications, ranging from direct restorative materials, to intermediary dental materials such as liners, bases, and luting cement, to preformed structure for dental and osseous tissue repair applications. Yet further, it is an object of the present invention to provide such a composition which may advantageously be used for implants and/or tissue scaffolding (growing natural tissue within/on a porous synthetic material). It is still further an object of the present invention to provide such a composition which advantageously provides continuous fluoride release.

SUMMARY OF THE INVENTION

The present invention addresses and solves the above-mentioned problems and meets the enumerated objects and advantages, as well as others not enumerated, by providing ionomer composite compositions useful for dental applications. The composition consists essentially of a glass material containing at least one of divalent cations and multivalent cations, and optionally containing fluoride; and at least one copolymer. The copolymer comprises at least one hydrophilic monomer containing acid functional groups adapted to react with the divalent cations and/or multivalent cations to form ionic crosslinks among polymer chains. The hydrophilic monomer is present in an amount sufficient to impart a desired degree of aqueous solubility to the copolymer. The copolymer further comprises at least one hydrophobic monomer present in an amount sufficient to impart a desired degree of structural stability to the composite composition when exposed to an aqueous environment.

The present ionomer composite composition is particularly advantageous in that, by varying the ratio of hydrophilic monomer to hydrophobic monomer, the copolymer may vary from water soluble to water insoluble. Thus, the present ionomer composite composition may be used for a wide variety of dental applications, ranging from those requiring water soluble compositions, eg. direct restorative materials, to intermediary materials such as for example, liners, bases, and luting cement, to those requiring water insoluble compositions, eg. to fabricate preformed structure for dental and osseous tissue repair applications.

BRIEF DESCRIPTION OF THE DRAWINGS

Other objects, features and advantages of the present invention will become apparent by reference to the following detailed description and drawings, in which.

DETAILED DESCRIPTION OF THE PREFERRED EMBODIMENTS

The present invention provides novel ionomer composite compositions fortuitously useful for a heretofore unexpectedly wide range of dental applications. Such applications may range from direct restorative materials, eg. cure-in-mouth cements, to intermediary materials such as for example, liners, bases and luting cement, to preformed structure for dental and osseous tissue repair applications.

It is also to be understood that the present inventive compositions may find uses outside of the dental field, such as in orthopedic applications. Further, the fluoride releasing agent may be eliminated, if desired, from the copolymer-glass ionomeric composition described further hereinbelow; and the ionomeric composition(s) may find use as structural materials.

The present novel and inventive composition does not lie on the established continuum (discussed hereinabove) between conventional glass ionomers, resin-modified glass ionomers, polyacid-modified composite resins (compomers), and composite resins. Rather, the novel composite compositions of the present invention possess unique properties.

The composition consists essentially of a glass material containing at least one of fluoride, divalent cations and multivalent cations; and at least one copolymer. The copolymer comprises at least one hydrophilic monomer containing acid functional groups adapted to react with the divalent cations and/or multivalent cations to form ionic crosslinks among polymer chains. The hydrophilic monomer is present in an amount sufficient to impart a desired degree of aqueous solubility to the copolymer. The copolymer further comprises at least one hydrophobic monomer present in an amount sufficient to impart a desired degree of structural stability to the composite composition when exposed to an aqueous environment.

It is to be understood that any suitable glass particles/materials may be chosen which contain divalent or/and multivalent cations. The glass material(s) optionally may contain fluoride(s). In a preferred embodiment, the glass material is selected from the group consisting of $SiO_2$, $Al_2O_3$, $AlF_3$, $CaF_2$, $NaF$, $Na_3AlF_6$, $AlPO_4$, and mixtures thereof. If a combination of these glass materials is chosen, such materials may be advantageously combined at various ratios.

The glass to polymer weight ratio may be between about 1:99 and about 95:5. In a preferred embodiment, the glass to polymer weight ratio is between about 10:90 and about 90:10. Still more preferred, the glass to polymer weight ratio is between about 40:60 and about 85:15.

It is to be understood that the composition of the present invention may comprise a copolymer or copolymers of two or more types of monomers, provided that at least one monomer is hydrophilic and at least one monomer is hydrophobic.

In accordance with the present invention, it is to be understood that any hydrophilic monomer(s) may be chosen provided it contains the above-mentioned acid functional groups adapted to react with the glass material(s)' divalent cations and/or multivalent cations to form ionic crosslinks among polymer chains. The acid functional groups also may react with calcium ions in teeth, leading to a desirable increase in the composition's adhesion properties with respect to the teeth.

Some example suitable acid-containing hydrophilic monomers include the following: 1) Monomers containing carboxylic acid: acrylic acid, methacrylic acid, 4-vinylbenzoic acid, crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentenoic acid, other unsaturated carboxylic acids, anhydrides, their derivatives, and mixtures thereof; 2) Other organic acids such as sulfonic acid, and/or phosphonic acid replacement of the carboxyl group of the above listed unsaturated carboxylic acids, their derivatives, and mixtures thereof.

In addition to the one or more hydrophobic monomers and the one or more acid-containing hydrophilic monomers in the present inventive co-polymer composition, other hydrophilic monomers that do not have a reactive carboxyl group may be used as a co-monomer within the present inventive composition. An example of such a non-acid-containing hydrophilic monomer is 2-hydroxyethyl methacrylate (HEMA).

It is to be understood that, in accordance with the present invention, any hydrophobic monomer may be chosen, provided it imparts the desired degree of structural stability to the composite composition when exposed to an aqueous environment.

Some exemplary suitable hydrophobic unsaturated monomers include the following: acrylates, methacrylates (eg. methyl methacrylate), ethylene, propylene, tetra-fluoroethylene, styrene, vinyl chloride, vinylidene chloride, vinyl acetate, acrylonitrile, 2,2-bis[4-(2-hydroxy-3-methacryloyloxy-propyloxy)-phenyl]propane (Bis-GMA), ethyleneglycol dimethacrylate (EGDMA), tri-ethyleneglycol dimethacrylate (TEGDMA), bis(2-methacryly-oxyethyl) ester of isophthalic acid (MEI), bis(2-meth-acryloxyethyl) ester of terephthalic acid (MET), bis( 2-methacryloxyethyl) ester of phthalic acid (MEF), 2,2-bis(4-methacrylyoxy phenyl) propane (BisMA), 2,2-bis[4-(2-methacrylyloxyethoxy) phenyl]propane (BisEMA), 2,2-bis[4-( 3-methacrylyloxypropoxy)phenyl]propane (BisPMA), hexafluoro-1,5-pentanediol dimethacrylate (HFPDMA), bis-(2-methacrylyloxyethoxy-hexafluoro-2-propyl)benzene [Bis(MEHFP)φ], 1,6-bis(methacrylyloxy-2-ethoxycarbonylamino)-2,4,4-tri-methylhexane (UEDMA), spiro orthocarbonates, other vinyl monomers, the derivatives of these monomers, and mixtures thereof.

The ratio of the hydrophilic monomeric units to the hydrophobic monomeric units may vary between about 1:99 and about 99:1. In a preferred embodiment, the hydrophilic monomer to hydrophobic monomer ratio is between about 5:95 and 95:5. By varying the monomer ratio, the copolymer could vary from water soluble (suitable for direct restorative dental applications) to water insoluble (suitable for fabrication of preformed dental structure and the like). As the amount of hydrophilic monomer is increased, the copolymer (as well as the ionomer composite composition) becomes more water soluble.

It is to be understood that any combination of the above hydrophilic and hydrophobic monomers may be suitable to form the copolymer component according to the present invention. An exemplary list of some copolymers includes the following: poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylonitrile-maleic anhydride), poly(butadiene-acrylonitrile-acrylic acid), poly(butadiene-maleic acid), poly(butadiene-maleic anhydride), poly(propylene-acrylic acid), poly(propylene-ethylene-acrylic acid), poly(vinyl chloride-vinyl acetate-maleic acid), and mixtures thereof.

It is to be understood that the copolymers in the ionomer composite systems of the present invention may be polymerized before, during or after the ionomer reactions (base-acid reactions). In a preferred embodiment, the polymers or copolymers are polymerized before the ionomer reaction in order to reduce the contents of unreacted monomers or oligomers to improve biocompatibility.

According to the present invention, there may be a mixture of one or more of the above-mentioned copolymers; and other polymers in minor amounts may be added to the ionomer composite systems of the present invention. Examples of some such polymers which may be present as minor components include, but are not limited to poly (methyl methacrylate) (PMMA), polycarbonates, polyethylenes, polyamides, poly(ether-ether ketone) (PEEK) polymers, epoxies, and mixtures thereof.

It is to be understood that the copolymers and/or polymers mentioned above may be obtained from a commercial source; or they may be synthesized from appropriate monomer(s). If they are synthesized, the monomer(s) are suitably polymerized. The synthesized polymer/copolymer is then preferably subjected to a purification step in order to remove any unreacted monomer(s). The copolymer and polymer(s) in minor amounts (if any) may then be mixed and reacted with glass particles as described further hereinbelow.

It is further contemplated as being within the purview of the present invention to include other minor components in the ionomer composite composition(s) of the present invention. For example, pigments, surfactants, adhesion enhances, fluoride releasing enhancers, and bioactive agents, such as for example, growth factors and hormones, and mixtures thereof may be incorporated thereinto if desired.

According to the present invention, the glass particles and the copolymers are mixed and reacted to form ionomer composite materials/compositions. The fluoride-containing glass particles can be dissolved or partially dissolved in a mixture of a water and organic solvent(s), or in an aqueous solution. The dissolved divalent and multivalent cations form ionic bonds with the acid groups on the copolymer to impart the system with the characteristics of a glass ionomer. The undissolved glass particles act as a reinforcing second phase. This fourtuitous result stemming from the present novel ionomeric composite composition is in contrast to the generally accepted theory (discussed hereinabove) that glasses are too weak and brittle to provide satisfactory reinforcement to dental restorative materials.

When polymerizable monomers, oligomers, and initiators are involved, a reinforcing polymerization may be carried out after the glass ionomer reaction, either thermally or photo-chemically, depending on the initiator type. The mechanical properties such as strength, moduli such as shear modulus, compressive modulus and tensile modulus, and hardness may be adjustable by varying the polymer composition and glass content.

The ionomer composite materials of the present invention may advantageously be thermally molded or solution cast to fabricate preformed structure for dental and osseous tissue repair applications. In addition, the present invention materials may also be used for applications of traditional glass ionomers and resin composites. As such, the present invention materials may be particularly adapted for use for inlays, onlays, artificial teeth, denture base, filling materials, cavity liner, adhesive, orthodontic resin, pit and fissure sealant, dental, orthopedic and bone implants.

Further advantages flow from the ion releasing properties, which may impart the inventive materials with desirable bioactivities. Of specific importance is the fluoride release that can prevent secondary caries and reduce plaque formation in dental applications.

A preferred embodiment useful for preformed dental structure comprises a novel glass ionomer: poly(methyl methacrylate-co-methacrylic acid) (PMMA-MAA) glass ionomer. This material differs from standard glass ionomers in that the copolymer, in certain hydrophilic monomer to hydrophobic monomer ratios, is not water soluble, thereby reducing undesirable reaction with the oral environment. It also differs from PMMA based ionomers (see, for example, Ma, X., J. A. Sauer, et al., "Poly(methyl methacrylate) Based Ionomers. 1. Dynamic Mechanical Properties and Morphology," *Macromolecules* 28(11): 3953–3962 (1995)) by utilizing glass as a reinforcing second phase and ions from the glass in the crosslinking.

It has been fortuitously found that, by employing a PMMA-MAA copolymer, both the advantages of the methyl methacrylate unit and the ionomer character of the methacrylic acid unit work in combination to form a strong and soundly crosslinked structure.

The glass was chosen for its fluoride release capabilities. See, for example, Kent, B., B. Lewis, et al., "Glass Ionomer Cement Formulations: I. The Preparation of Novel Fluoroaluminocilicate Glasses High in Fluorine," *Journal of Dental Research* 58(6): 1607–1619 (1979); Wilson, A. D., S. Crisp, et al., "Aluminocilicate Glasses for Polyelectrolyte Cements," *Ind. Eng. Chem. Prod. Res. Dev.* 19: 263–270 (1980); de Araujo, F. B., F. Garcia-Goody, et al., "Fluoride release from fluoride-containing materials," *Operative Dentistry* 21: 185–190 (1996); Forsten, L., "Fluoride release and uptake by glass-ionomers and related materials and its clinical effect," *Biomaterials* 19: 503–508 (1998); and Verbeeck, R. M. H., E. A. P. De Maeyer, et al., "Fluoride release process of (resin-modified) glass-ionomer cements versus (polyacid-modified) composite resins," *biomaterials* 19:509–519 (1998).

In a preferred embodiment, the polymeric component of the composite composition comprises a copolymer, as opposed to a monomer(s), oligomers, or a completely water soluble polymer(s). This is preferable to in situ polymerization of a monomer(s), in that unreacted monomers remaining in the patient's mouth may have a deleterious effect on the mechanical properties of the dental restorative material, as well as on the patient's health.

As shown below in the Examples, the addition of glass to the PMMA-MAA copolymer appears to increase the compressive modulus, yield strength, and hardness of the material. It is believed that the improvement is no longer significant above about 70 weight % glass due, at least in part, to a limit in the packing density.

It appears that samples containing a greater amount of methacrylic acid units possess better mechanical properties within the copolymer range studied below (up to 25%) due, at least in part, to the larger number of crosslinks.

Without being bound to any theory, it is believed that the ionic interactions, both the polymer-polymer crosslinking and the polymer-glass ionic bonding, contribute to the increase in mechanical properties of the PMMA-MAA glass ionomer material.

Further, as can be seen below, experimental data indicate that the PMMA-MAA glass ionomer material is capable of sustained fluoride release.

To further illustrate the composition, the following examples are given. It is to be understood that these examples are provided for illustrative purposes and are not to be construed as limiting the scope of the present invention.

These initial studies evaluate PMMA-MAA glass ionomers using both hardness and compression testing.

EXAMPLE 1

Glass Incorporation. Two sets of samples were prepared for testing. In the first group, an 80:20 PMMA-MAA random copolymer was used with the following glass contents: 0.00, 6.25, 14.29, 25.00, 33.33, 40.00, 45.45, 50.00, 60.53, 70.00, and 80.00 weight percent. The second set includes the following PMMA-MAA random copolymers: 75:25, 80:20, 95:5, and 100:0, containing 0 wt % and 50 wt % glass. The copolymers were obtained from Polysciences, Inc., Warrington, Pa., the PMMA from Sigma Chemical Co., St. Louis, Mo., and the glass from Specialty Glass Inc., Oldsmar, Fla., with a composition of 25.10 wt % $SiO_2$, 37.45 wt % $Al_2O_4$, and 37.45 wt % $CaF_2$. The glass particles are irregular in shape, range from 1–20 microns, and have no surface treatment.

To incorporate the glass, the polymer was dissolved at a $1/12$ g/ml ratio in a 20% methanol, 80% benzene solution. For the 75:25 copolymer it was necessary to use a 30:70 solvent mix. The polymer and solvent were placed in a vial and vibrated on a shaker overnight. After 24 hours, the glass and a stir bar were added, and the mixture was stirred for one hour to incorporate the glass and allow time for the glass ionomer reaction to occur. The sample was frozen in a −20° C. freezer, then placed on a lyophilizer in ice/salt bath to remove the solvent. A liquid nitrogen solvent trap was maintained for two days, and the samples allowed to stay on the lyophilizer for a total of seven days.

EXAMPLE 2

Compression Molding Process. The following protocol was used to make samples for hardness and compression testing. A 4 mm diameter compression mold was filled with from 0.2 g to 0.3 g of sample (obtained by the procedure of Example 1). The sample amount was varied due to the density difference between the filled and unfilled polymer. The mold was placed in an oven at 450° F. for two hours, then moved to a preheated 420° F. press. The plunger was pressed down with 2000 lbs. force which was applied for 45 minutes, being monitored every 15 minutes, and increased if it had fallen. The pressure was then released and the plunger removed. This sample was allowed to stay on the press at 420° F. for another 45 minutes to remove any residual compressive stresses. At this time the heater was turned off, and the sample cooled to room temperature before being removed from the mold.

EXAMPLE 3

Compression Testing. The cylindrical samples prepared in the compression mold of Example 2 were ground so that the ends were parallel. All samples possessed a length to diameter (L/D) ratio of 2.5. The samples were compressed to failure using a compression jig on an Instron 8521 mechanical tester with a crosshead speed of 0.5 mm/min. Five specimens were tested for each data point.

EXAMPLE 4

Hardness Testing. Samples prepared as in Example 2 were placed in liquid nitrogen and fractured with a hammer. A fragment no less than 2 mm thick was ten mounted in Kould Mount. These samples were ground to 600 grit silicon carbide followed by polishing with a one micron diamond paste. A Tukon Microhardness Tester, model LR, was used to produce and measure Vickers indents using a 300 g load. Three indents were made on each sample and averaged.

EXAMPLE 5

Ion Bonding Test. In order to ascertain the effect of ions leached from the glass in crosslinking the polymer, an additional test was done. Glass powder was placed in a 20:80 methanol/benzene solvent mix (a 30:70 solvent mix for the 75/25 copolymer) and stirred for one hour. The glass was removed by centrifuging for one minute and decanting off the "ion solvent". This "ion solvent" was then used to prepare 0% glass PMMA-MAA compression and hardness samples as described above for each of the copolymers.

EXAMPLE 6

Fluoride Release Test. Five glass ionomer samples 1 cm×1 cm×0.05 cm were made for all fourteen variations (see Example 7 below) of the material, including the different glass contents and the different copolymers containing 50 wt % glass. Each sample was placed in a vial containing 5 ml $ddH_2O$. These samples were maintained on a shaker at 37° C. for the duration of the experiment. Each day the water was removed for fluoride measurement, and fresh water was placed in the sample vial. The aliquots were measured on an Orion Model 720A pH meter, using an Orion $F^-$ detector, Model 96-09. Using a fluoride standard solution, the meter was referenced at 1, 0.1, and 0.01 ppm. The ionic strength of each sample, and the standards, were adjusted with TISAB II buffer just prior to measurement. This method is similar to that used by other researchers (de Araujo, Garcia-Goody et al. 1996; Verbeeck, De Maeyer et al. 1998). Measurements were made on days 1, 2, 3, 4, 5, 7 and 14.

EXAMPLE 7

Fluoride Release Test. Two sets of samples were prepared for testing. In the first group, an 80:20 PMMA-MAA random copolymer was used with the following glass contents: 0.00, 6.25, 14.29, 25.00, 33.33, 40.00, 45.45, 50.00, 60.53, 70.00 and 80.00 weight %. The second set includes the following PMMA-MAA random copolymers: 75:25, 80:20, 95:5 and 100:0, containing 0 weight % and 50 weight % glass. The copolymers were obtained from Polysciences, Inc., Warrington, Pa., the PMMA from Sigma Chemical Co., St. Louis, Mo., and the glass from Specialty Glass Inc., Oldsmar, Fla., with a composition of 25.10 wt % $SiO_2$, 37.45 wt % $Al_2O_3$, and 37.45 wt % $CaF_2$. The glass particles are irregular in shape, range form 1–20 microns, and have no surface treatment. The glass was incorporated into the copolymer as described hereinabove in Example 1.

Five glass ionomer samples 1 cm×1 cm×0.05 cm were made using a high temperature compression system for all fourteen variations of the material, including the different glass contents and the different copolymers containing 50 wt % glass. Each sample was placed in a vial containing 5 ml $ddH_2O$. These samples were maintained on a shaker at 37° C. for the duration of the experiment. Each day the water was removed for fluoride measurement, and fresh water was placed in the sample vial. The aliquots were measured on an Orion Model 720A pH meter, using an Orion F detector, Model 96-09. Using a fluoride standard solution, the meter was referenced at 1, 0.1, and 0.01 ppm. The ionic strength of each sample, and the standards, were adjusted with TISAB II buffer just prior to measurement. Measurements were made on days 1, 2, 3, 4, 5 and 7.

Discussion of Experimental Results

Figure 1:
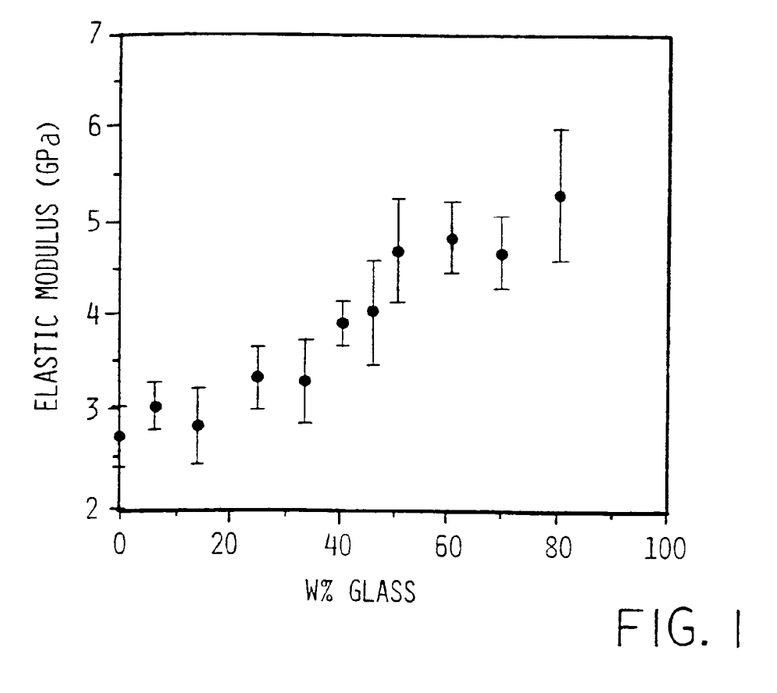
FIG. 1 is a graph showing compressive modulus data for an 80:20 PMMA-MAA copolymer having varying glass contents.

Effects of glass content on mechanical properties. FIG. 1 shows the compressive modulus data for the glass filled 80:20 polymer. The elastic modulus is comparable to that of the best commercial glass ionomer materials available (O'Brien 1997). A sigmoidal trend is observed, with the modulus remaining nearly the same until a critical glass percentage is reached, at which the modulus increases rapidly. At high glass content, another critical glass percentage is attained where additional glass no longer improves the modulus. It is believed that, upon optimization of the compositions of the present invention, even better modulus data may be obtained, thereby surpassing that of the best available commercial glass ionomer materials.

Figure 2:
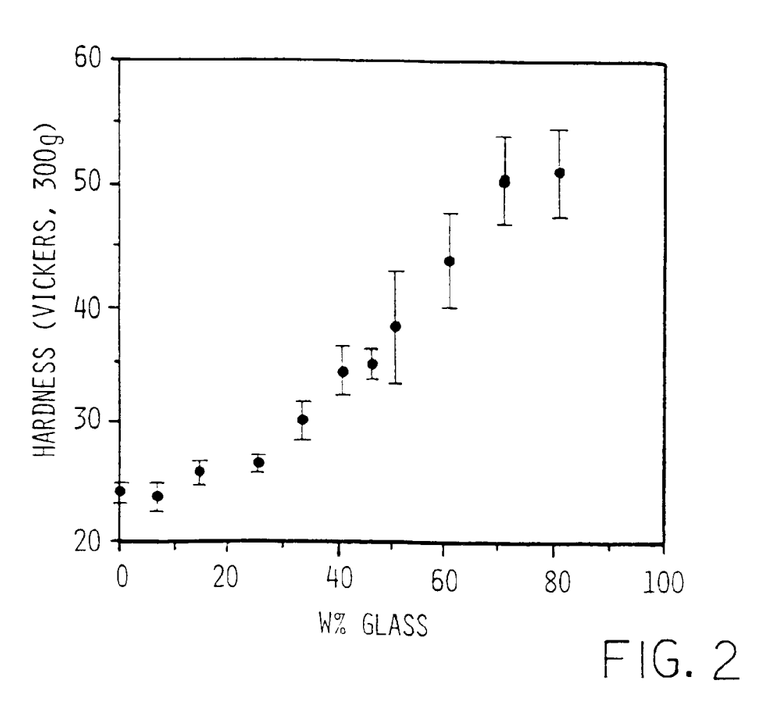
FIG. 2 is a graph showing Vickers hardness data for the glass filled 80:20 PMMA-MAA copolymers.

Similar to the compressive modulus data, the Vickers hardness of the material shows a sigmoidal trend with increased glass content (FIG. 2). These values compare favorably to those of commercially available glass ionomers and dentin tooth structure (O'Brien 1997). As with the modulus data, it is believed that, upon optimization of the compositions of the present invention, even better hardness data may be obtained, thereby surpassing that of commercially available glass ionomer materials.

In the PMMA-MAA glass ionomer, the carboxyl group on the methacrylic acid unit is able to bind with $Ca^{+2}$ and $Al^{+3}$ ions from the glass. Some of these ions are presumably leached out of the glass during the reaction creating crosslinking between polymer chains, and also forming links between the ionomer and the glass itself. This produces a polymeric matrix filled with glass particles surrounded by ionic aggregates. Without being bound to any theory, it is believed that, by developing these ionic interactions between the glass particles and the polymer matrix, the mechanical properties of the material are increased.

When interpreting the strength data, it has been found in the present invention that it may be beneficial to consider several interactions. Some of the mechanical properties of the material may be attributed to a mechanical interaction between glass particles. The glass and polymer packing density may also play an important role in the analysis of the data at high glass contents. In addition, it has been found that three chemical interactions may come into play: the polymer-glass ionic bonding, the polymer-polymer ionic bonding, and the polymer-polymer hydrogen bonding.

If the interactions mentioned above are considered in the compression modulus data interpretation, it can be seen that the glass-glass mechanical contact appears to dominate the modulus trend. As more glass particles are added to the material, it becomes less pliable and therefore more resistant to being compressed. Modulus is related to very small deformation, so at low glass contents, the particles are not forced to touch each other, showing little change in the modulus. Once a critical glass content is reached, the modulus increases rapidly. At about 50 wt % glass, the material assumes a continuous glass structure with the particles touching, and the resistance to being compressed levels off. At high glass content the effect of packing density comes into consideration. Since the glass possesses a range of sizes, the packing is improved over particles of all one size. See, for example, Cross, M., W. H. Douglas, et al., "The Relationship Between Filler Loading and Particle Size Distribution in Composite Resin Technology," *Journal of Dental Research* 62(7): 850–852 (1983).

At a certain packing density, it appears that additional glass does not increase the number of glass-glass particle contacts, thus not longer improving the mechanical properties of the material. Other researchers have seen a linear increase of modulus as the glass content is increased in a glass-filled PMMA composite material. See, for example, Soderholm, K.-J., "Relationship between compressive yield strength and filler fractions of PMMA composites," *Acta Odontol. Scand.* 40: 145–150 (1982). However their data do not cover as wide of a glass range.

Figure 3:
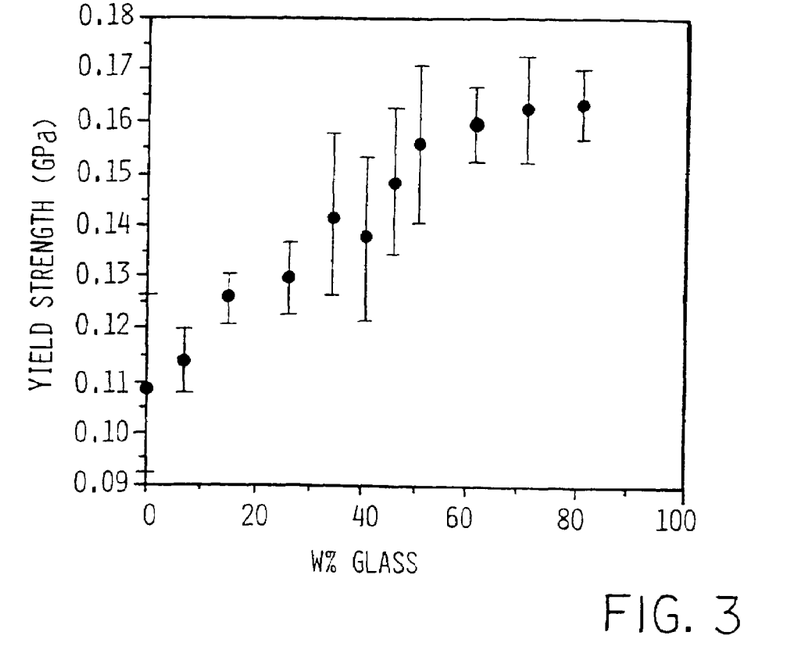
FIG. 3 is a graph showing yield strength data for the glass filled 80:20 PMMA-MAA copolymers.

FIG. 3 exhibits the yield strength data for the 80:20 copolymer with glass filler. There is a linear increase in yield strength to approximately 60 wt % glass, wherein it then levels off. Unlike the modulus data, the yield strength at low glass content increases linearly starting at 0 wt % glass. It is believed that this is due to the fact that yield strength is a function of larger strain than the modulus, and the glass particles are forced to touch as the material yields. Other researchers have seen a linear increase in yield strength for a glass filled PMMA, for both silane treated and untreated glass. See, for example, Soderholm (1982); and Krause, W. R., S.-H. Park, et al., "Mechanical properties of BIS-GMA resin short glass fiber composites," *Journal of Biomedical Materials Research* 23: 1195–1211 (1989). It is believed that the packing density discussed above is most likely responsible for the bend in the yield strength curve at high glass content.

Figure 4:
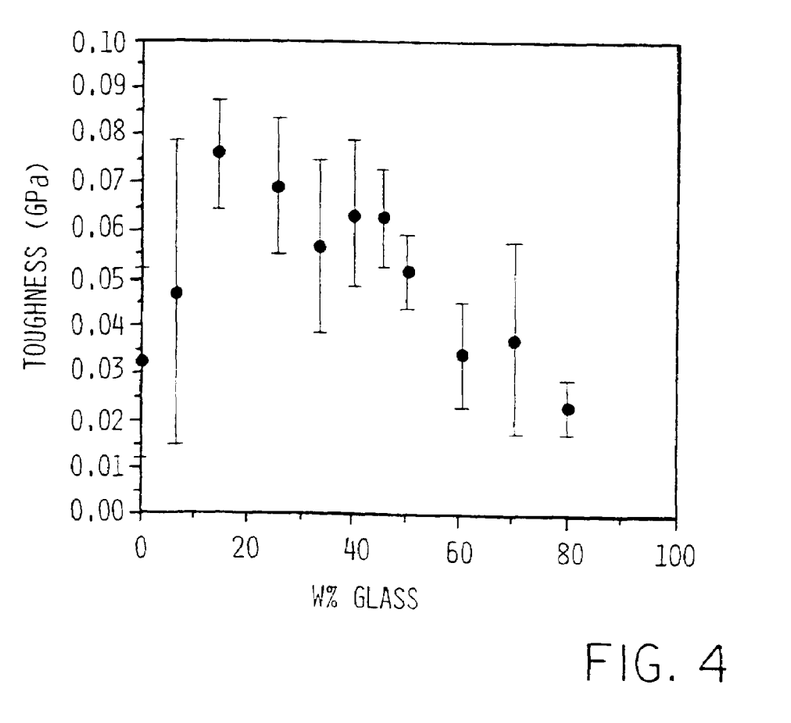
FIG. 4 is a graph showing toughness data for the glass filled 80:20 PMMA-MAA copolymers.

The toughness data is shown in FIG. 4. The addition of glass improved the toughness of 80:20 PMMA-MAA at glass concentrations below 70 wt % glass. The peak appears around about 15–20 wt % glass.

Figure 5:
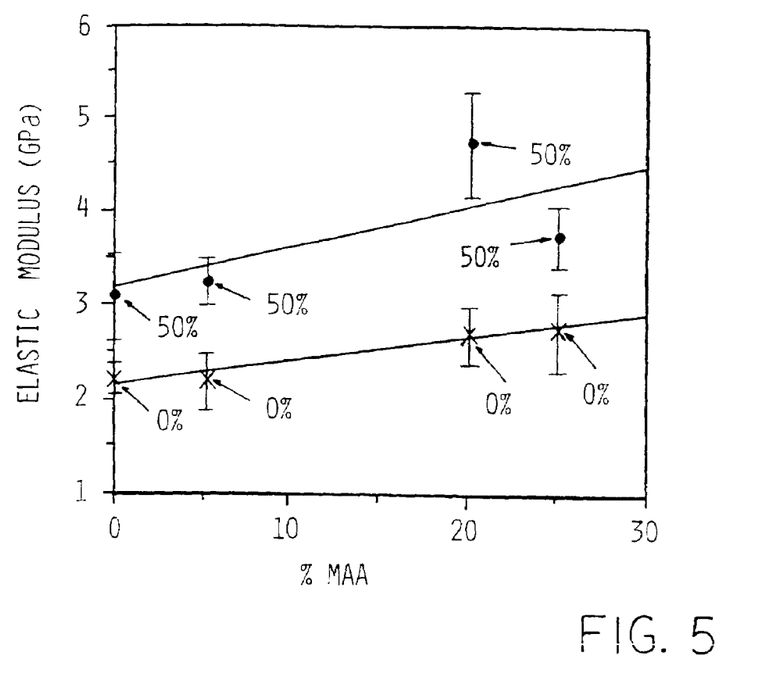
FIG. 5 is a graph showing modulus data for PMMA-MAA copolymers having varying MAA percentages, with 0 weight % and 50 weight % glass.
Figure 6:
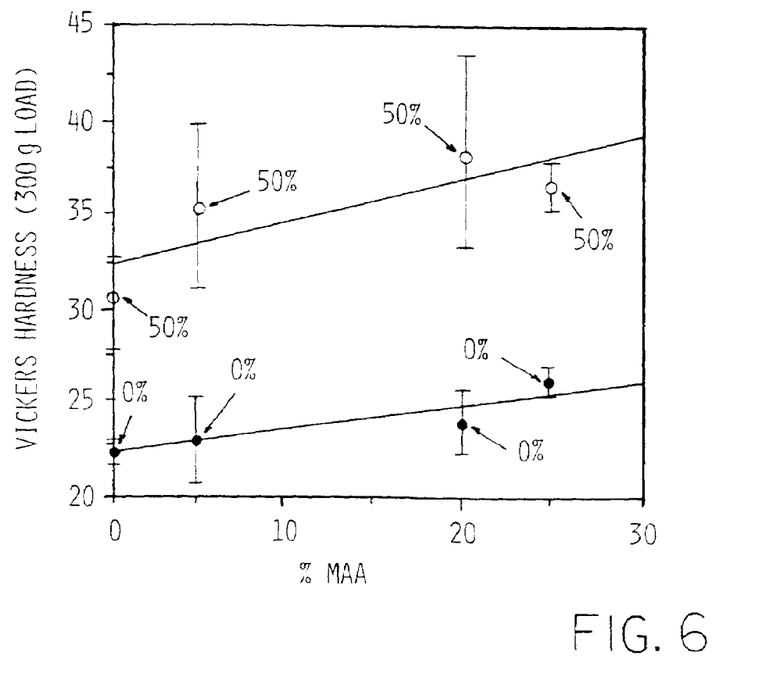
FIG. 6 is a graph showing Vickers hardness data for PMMA-MAA copolymers having varying MAA percentages, with 0 weight % and 50 weight % glass.

Effects of copolymer compositions on mechanical properties. Examination of FIG. 5 shows the elastic modulus data for PMMA-MAA copolymers with 0 wt % and 50 wt % glass. An increase in the methacrylic acid component of the copolymer increases the modulus of the material, as does the addition of glass filler. The Vickers hardness data show a similar trend (See FIG. 6).

Figure 7:
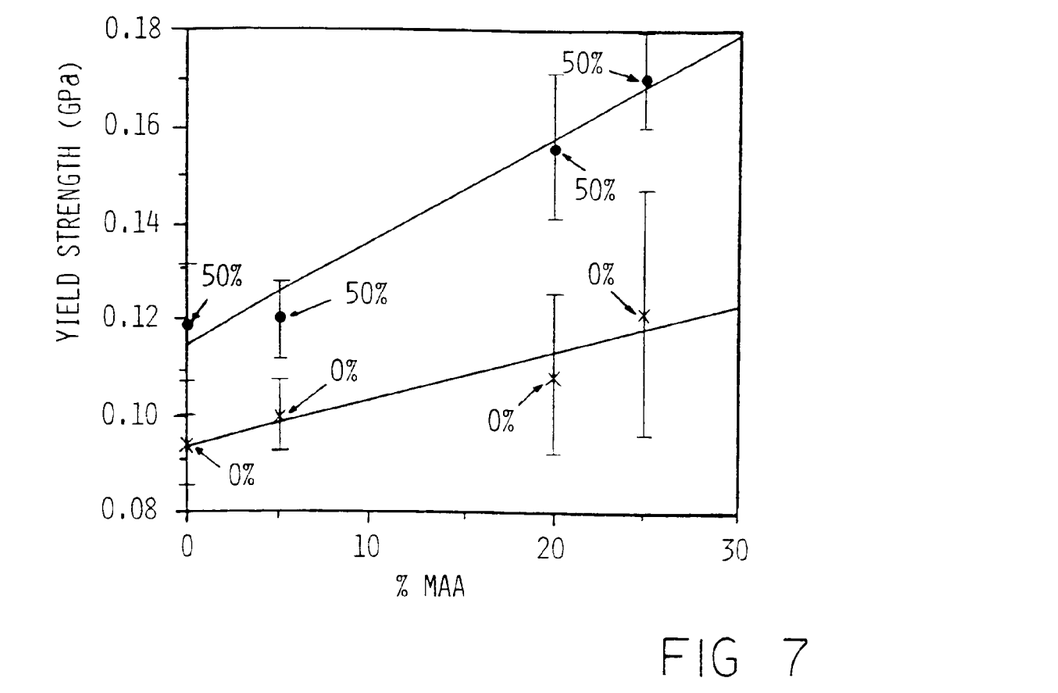
FIG. 7 is a graph showing yield strength data for PMMA-MAA copolymers having varying MAA percentages, with 0 eight % and 50 weight % glass.

In FIG. 7, the yield strength data for the PMMA-MAA glass ionomers are displayed. There is an increase in yield strength with an increases in MAA monomers. There is also an increase in yield strength with the addition of 50 wt % glass. There is a significant divergence in the two sets of data at higher ionomer content. The linear increase in yield strength with increase in MAA content (0 wt % glass) is presumably due to a greater number of hydrogen bonds between the chains. It is believed that the fact that the glass ionomers with 50 wt % glass have higher yield strengths than those of the corresponding copolymers (0 wt % glass) can be attributed to the glass-glass mechanical interactions. It is further believed that the divergence between 0 wt % and 50 wt % glass samples in the increasing rate (slope) of yield strength wit MAA content shows the synergism of the glass filler and ionic interactions—both the ionic links between polymer chains caused by the leached ions and the ionic links between the polymer chains and the glass fragments.

Figure 8:
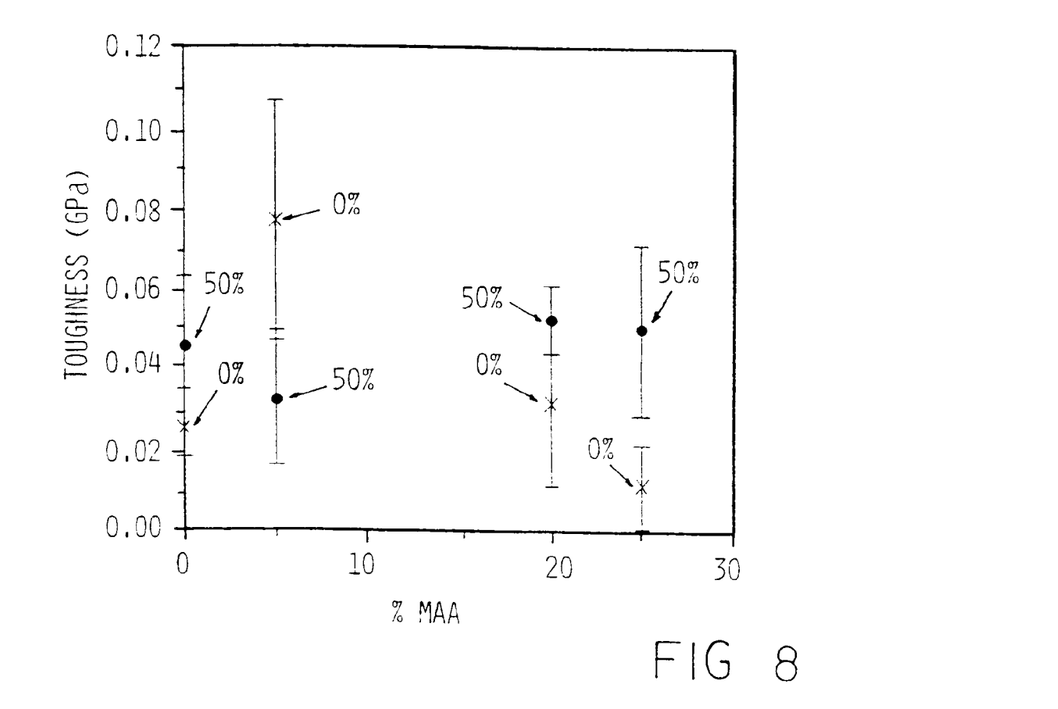
FIG. 8 is a graph showing toughness data for PMMA-MAA copolymers having varying MAA percentages, with 0 weight % and 50 weight % glass.

The toughness data are shown in FIG. 8. For MAA concentrations of 25%, 20%, and 0%, the addition of 50 wt % glass appeared to improve the toughness of the copolymer. The copolymer sample containing 5% MAA with 0 wt % glass appears to have a higher toughness than a similar sample with 50 wt % glass—this appeared to be an aberrant test result, and the present inventors plan to repeat this experiment.

Figure 9:
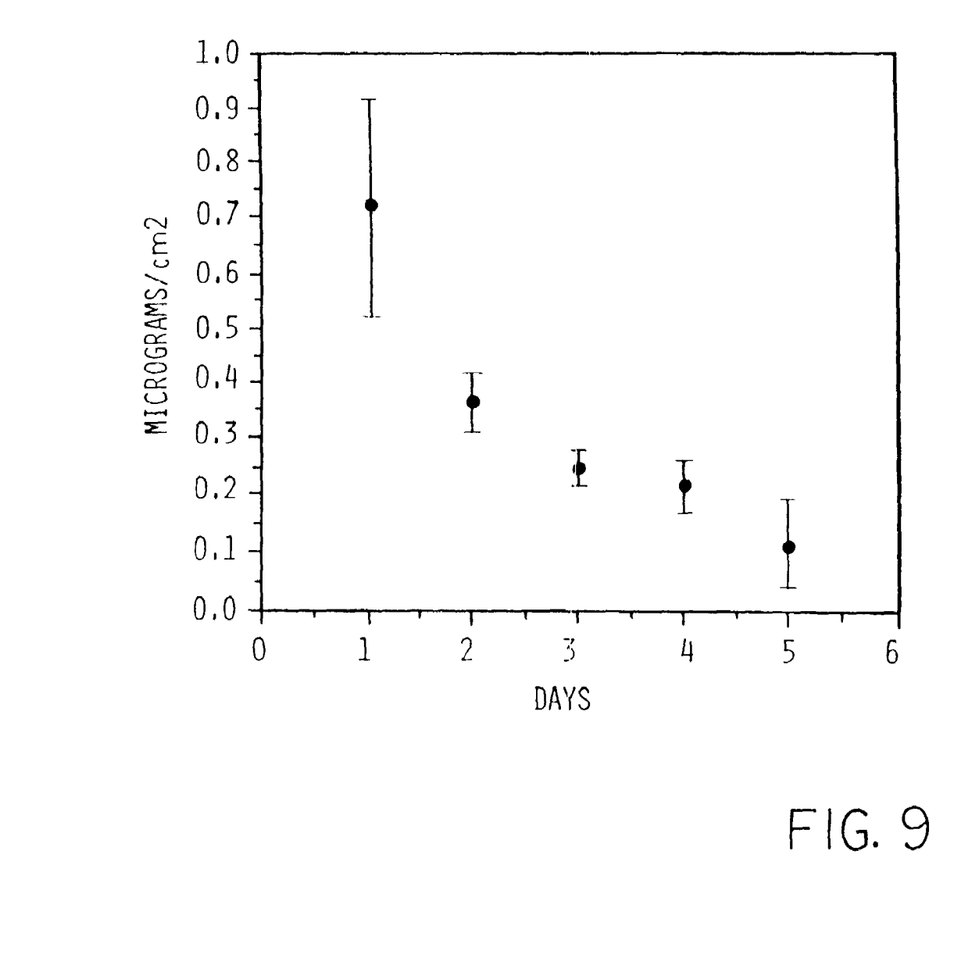
FIG. 9 is a graph showing fluoride release data for a 75:25 PMMA-MAA copolymer having 50 weight % glass.
Figure 10:
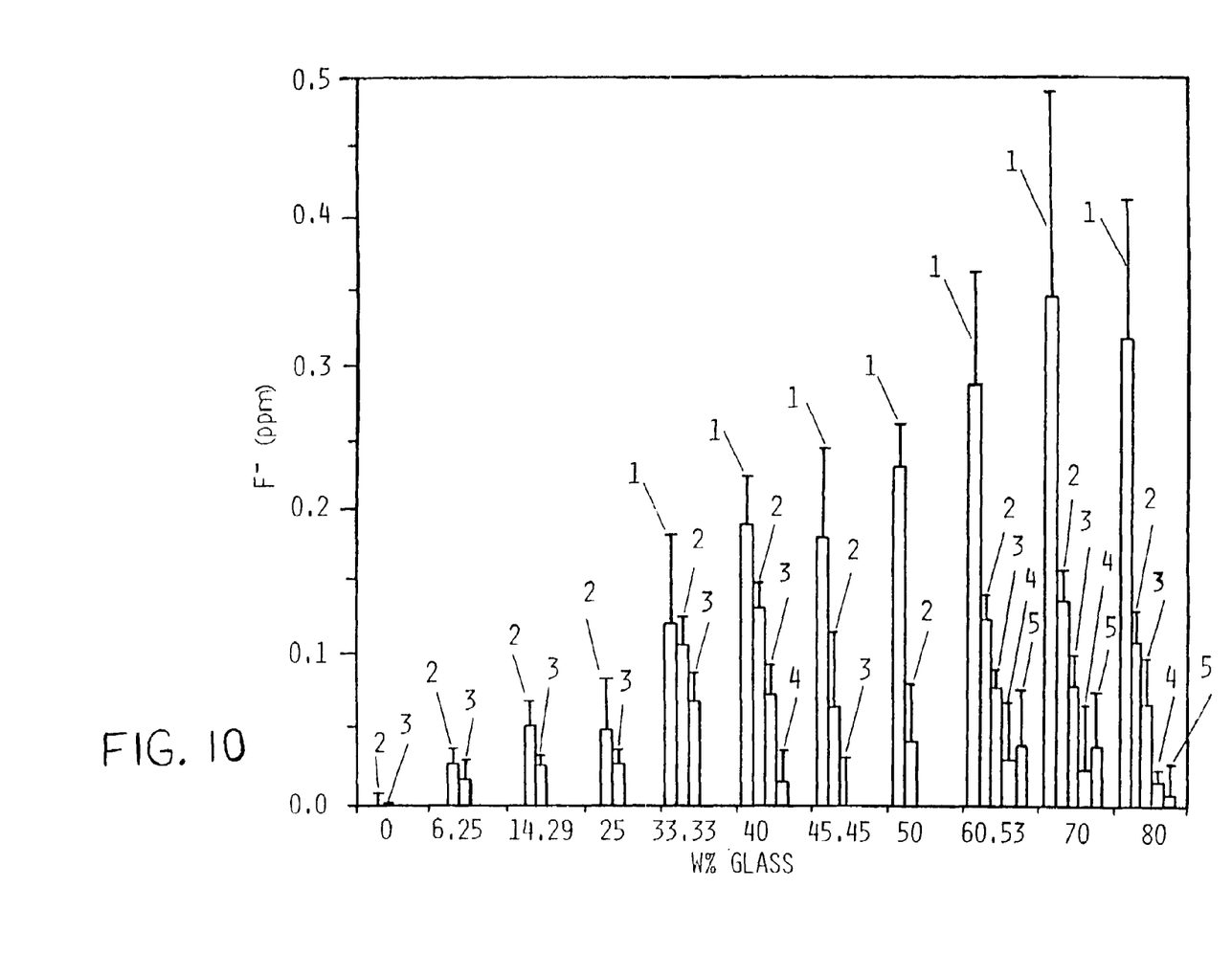
FIG. 10 is a graph showing fluoride release data for an 80:20 PMMA-MAA copolymer having from 0 weight % to 80 weight % glass.

Fluoride Release. The results of the fluoride release testing are shown in FIGS. 9 and 10. There is an initial burst release that tapers off with time. This profile is typical for glass ionomers materials. This is important for the initial blocking of caries development. Overall, the plot shows that with an increase in glass content, there is an increase in fluoride release, allowing for fine-tuning of the amount of fluoride released into the oral environment.

Examination of how the fluoride release is affected by copolymer composition shows that there is an increase in the release rate with a greater MAA content. The MAA component affects the material in two ways. It possesses the chemical unit which leaches the ions out of the glass. Therefore, a higher MAA content would indicate that more fluoride is available for release. Secondly, an increase in the MAA component makes the polymer slightly more susceptible to water attack. This would also create an increase in the fluoride release.

It is believed that, over a longer time, the unique ionomer composite composition of the present invention will advantageously provide continuous fluoride release.

As discussed hereinabove, the properties of the novel and unique ionomer composite composition of the present invention may easily be adjusted by altering the ratio of hydrophilic monomer to hydrophobic monomer in the copolymer, and/or by altering the glass content. Bonding between acid-containing hydrophilic monomers and glass particles, along with the monomer-monomer bonds are formed by acid leaching of cations from the glass particles, forming a strong interface between the filler and matrix. An added advantage of this ion leaching is that fluoride ions may also be released from the glass, if desired.

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined by the following claims.

What is claimed is:

1. An ionomer composite composition having improved physical properties, the composite consisting essentially of:
   a glass material containing divalent cations, multivalent cations, or combinations thereof; and
   at least one copolymer, comprising:
      at least one hydrophilic monomer containing acid functional groups adapted to react with the divalent cations, multivalent cations, or mixtures thereof to form ionic crosslinks among polymer chains, the hydrophilic monomer present in an amount sufficient to impart a desired degree of aqueous solubility to the copolymer, the hydrophilic monomer amount ranging from about 1% to about 25% of the copolymer; and
      at least one hydrophobic monomer present in an amount sufficient to impart a desired degree of structural stability to the composite composition when exposed to an aqueous environment, the hydrophobic monomer amount ranging from about 75% to about 99% of the copolymer;
   wherein the at least one copolymer is selected from the group consisting of poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylonitrile-maleic anhydride), poly(butadiene-acylonitrile-acrylic acid), poly(butadiene-maleic acid), poly(butadiene-maleic anhydride), poly(propylene-acrylic acid), poly(propylene-ethylene-acrylic acid), poly(vinyl chloride-vinyl acetate-maleic acid), and mixtures thereof.

2. The ionomer composite composition as defined in claim 1 wherein the glass material further contain fluoride, and wherein the composite composition provides fluoride release.

3. The ionomer composite composition as defined in claim 1 wherein the glass material is selected from the group consisting of $SiO_2$, $Al_2O_3$, $AlF_3$, $CaF_2$, $NaF$, $Na_3AlF_6$, $AlPO_4$, and mixtures thereof.

4. The ionomer composite composition as defined in claim 1 wherein a weight ratio of glass material to copolymer from about 10:90 to about 90:10.

5. The ionomer composite composition as defined in claim 4 wherein the weight ratio of glass material to copolymer ranges from about 40:60 to about 85:15.

6. The ionomer composite composition as defined in claim 1 wherein the at least one hydrophilic monomer is a monomer containing unsaturated carboxylic acid.

7. The ionomer composite composition as defined in claim 6 wherein the unsaturated carboxylic acid is selected from the group consisting of: acrylic acid, methacrylic acid, 4-vinylbenzoic acid crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentenoic acid, anhydrides of the acids, and mixtures thereof.

8. The ionomer composite composition as defined in claim 7 wherein the hydrophilic monomer is from the group consisting of organic acids having at least one of sulfonic acid and phosphonic acid replacement of the carboxyl group of the unsaturated carboxylic acids, and mixtures thereof.

9. The ionomer composite composition as defined in claim 1 wherein the at least one hydrophobic monomer is unsaturated.

10. The ionomer composite composition as defined in claim 9 wherein the at least one hydrophobic monomer is selected from the group consisting of acrylates, methacrylates, ethylenes, propylenes, tetra fluoroethylene, styrenes, vinyl chloride, vinylidene chloride, vinyl acetate, acrylonitrile, 2,2-bis-[4-(2-hydroxy-3-methacryloxyloxy-propyloxy)-phenyl] propane (Bis-GMA), ethyleneglycol dimethacrylate (EGDMA), tri-ethyleneglycol dimethacrylate (TEGDMA), bis(2-methacryly-oxyethyl) ester of isophthalic acid (MEI), bis(2-methyacryloxyethyl) ester of terephthalic acid (MET), bis(2-methacryloxyethyl) ester of phthalic acid (MEP), 2,2-bis(4-methacrylyoxy phenyl) propane (BisMA), 2,2-bis[4-(2-methacrylyloxyethoxy) phenyl] propane (BisEMA), 2,2-bis[4-(3-methacrylyloxy-propoxy) phenyl]propane (BisPMA), hexafluoro-1,5-pentanediol dimethacrylate (HFPDMA), bis-(2-methacrylyloxyethoxy-hexafluoro-2-propyl)benzene [Bis(MEHFP)ϕ], 1,6-bis(methacrylyloxy-2-ethoxycarbonylamino)-2,4,4-trimethyl-hexane (UEDMA), spiro orthocarbonates, and mixtures thereof.

11. The ionomer composite composition as defined in claim 1 wherein a ratio of the hydrophlic monomer to the hydrophobic monomer is from about 1:99 to about 20:80.

12. The ionomer composite composition as defined in claim 1 wherein the composite further includes as a minor constituent a polymer selected from the group consisting of PMMA, polycarbonates, polyethylenes, polyamides, PEEK polymers, epoxies, and mixtures thereof.

13. The ionomer composition as defined in claim 2 wherein the composite further includes a minor constituent selected from the group consisting of pigments, surfactants, adhesion enhancers, fluoride releasing enhancers, bioactive agents, and mixtures thereof.

14. The ionomer composition as defined in claim 2 wherein the glass material consists of 25.10 wt % $SiO_2$, 37.05 wt % $Al_2O_3$, and 37.45 wt % $CaF_2$.

15. An ionomer composite composition having improved physical properties, the composite consisting essentially of:
   a glass material containing divalent cations, multivalent cations, or combinations thereof; and
   at least one copolymer, comprising:
      at least one hydrophilic monomer containing acid functional groups adapted to react with the divalent cations, multivalent cations, or mixtures thereof to form ionic crosslinks among polymer chains, the hydrophilic monomer present in an amount sufficient to impart a desired degree of aqueous solubility to the copolymer, the hydrophilic monomer amount ranging from about 1% to about 25% of the copolymer; and
      at least one hydrophobic monomer present in an amount sufficient to impart a desired degree of structural stability to the composite when exposed to an aqueous environment, the hydrophobic monomer amount ranging from about 75% to about 99% of the copolymer;
   wherein the at least one copolymer is poly(methyl methacrylate co-methacrylic acid) (PMMA-MAA).

16. The ionomer composite composition as defined in claim 15 wherein the ratio of PMMA to MAA is 80:20.

17. An ionomer composite composition having improved physical properties and useful for dental applications, the composite consisting essentially of:
   a glass material containing divalent cations, multivalent cations, or combinations thereof; and
   at least one copolymer, comprising:
      at least one hydrophilic monomer containing acid functional groups adapted to react with the divalent cations, multivalent cations, or combinations thereof to form ionic crosslinks among polymer chains, the hydrophilic monomer present in an amount sufficient to impart a desired degree of aqueous solubility to the copolymer, the hydrophilic monomer amount ranging from about 1% to about 25% of the polymer; and
      at least one hydrophobic monomer present in an amount sufficient to impart a desired degree of structural stability to the composite composition when exposed to an aqueous environment, the hydrophobic monomer amount ranging from about 75% to about 99% of the copolymer;
   wherein the composite composition is adaptable for use in substantially water insoluble dental applications;
   and wherein the at least one copolymer is selected from the group consisting of poly(methyl methacrylate-methacrylic acid), poly(methyl acrylate-acrylic acid), poly(methyl methacrylate-acrylic acid), poly(ethyl acrylate-acrylic acid), poly(ethyl methacrylate-methacrylic acid), poly(butyl acrylate-acrylic acid), poly(ethylene-acrylic acid), poly(ethylene-methacrylic acid), poly(acrylonitrile-maleic anhydride), poly(butadiene-acylonitrile-acrylic acid), poly(butadiene-maleic acid), poly(butadiene-maleic anhydride), poly(propylene-acrylic acid), poly(propylene-ethylene-acrylic acid), poly(vinyl chloride-vinyl acetate-maleic acid), and mixtures thereof.

18. The ionomer composite composition as defined in claim 17 wherein the glass material further contains fluoride, and wherein the composite composition provides fluoride release.

19. The ionomer composite composition as defined in claim 18 wherein the glass material is selected from the group consisting of $SiO_2$, $Al_2O_3$, $AlF_3$, $CaF_3CaF_2$, NaF, $Na_3AlF_6$, $AlPO_4$, and mixtures thereof.

20. The ionomer composite composition as defined in claim 19 wherein the weight ratio of glass material to copolymer ranges from about 40:60 to about 85:15.

21. The ionomer composite composition as defined in claim 20 wherein the at least one hydrophilic monomer is an unsaturated carboxylic acid selected from the group consisting of: acrylic acid, methacrylic acid, 4-vinylbenzoic acid, crotonic acid, oleic acid, elaidic acid, itaconic acid, maleic acid, fumaric acid, acetylenedicarboxylic acid, tricarbollylic acid, sorbic acid, linoleic acid, linolenic acid, eicosapentenoic acid, anhydrides of the acids, and mixtures thereof.

22. The ionomer composite composition as defined in claim 21 wherein the at least one hydrophilic monomer is selected from the group consisting of organic acids having at least one of sulfonic acid and phosphonic acid replacement of the carboxyl group of the unsaturated carboxylic acids, and mixtures thereof.

23. The ionomer composite composition as defined in claim 21 wherein the at least one hydrophobic monomer is unsaturated and is selected from the group consisting of acrylates, methacrylates, ethylenes, propylenes, tetra-fluoroethylene, styrenes, vinyl chloride, vinylidene chloride, vinyl acetate, acrylonitrile, 2,2-bis[4-(2-hydroxy-3-methacryloyloxy-propyloxy)-phenyl]propane (Bis-GMA), ethyleneglycol dimethacrylate (EGDMA), tri-ethyleneglycol dimethacrylate (TEGDMA), bis(2-methacryly-oxyethyl) ester of isophthalic acid (MEI), bis(2-meth-acrylyoxyethyl) ester of terephthalic acid (MET), bis(2-methacrylyoxyethyl) ester of phthalic acid (MEP), 2,2-bis(4-methacrylyoxy phenyl) propane (BisMA), 2,2-bis[4-(2-methacrylyloxyethoxy) phenyl]propane (BisEMA), 2,2-bis[4-( 3-methacrylyloxypropoxy)phenyl]propane (BisPMA), hexafluoro-1,5-pentanediol dimethacrylate (HFPDMA), bis-(2-methacrylyloxyethoxy-hexafluoro-2-propyl)benzene [Bis(MEHFP)φ], 1,6-bis(methacrylyloxy-2-ethoxycarbonylamino)-2,4,4-tri-methylhexane (UEDMA), spiro orthocarbonates, and mixtures thereof.

24. The ionomer composite composition as defined in claim 23 wherein a ratio of the hydrophilic monomer to the hydrophobic monomer is from about 5:95 to about 20:80.

25. The ionomer composite composition as defined in claim 17 wherein the composite further includes as a minor constituent a polymer selected from the group consisting of PMMA, polycarbonates, polyethylenes, polyamides, PEEK polymers, epoxies, and mixtures thereof.

26. The ionomer composite composition as defined in claim 18 wherein the composite further includes a constituent selected from the group consisting of pigments, surfactants, adhesion enhancers, fluoride releasing enhancers, bioactive agents, and mixtures thereof.

27. The ionomer composite composition as defined in claim 18 wherein the glass material consists of 25.10 wt % $SiO_2$, 37.45 wt % $Al_2O_3$, and 37.45 wt % $CaF_2$.

28. An ionomer composite composition having improved physical properties and useful for dental applications, the composite consisting essentially of:

a glass material containing divalent cations, multivalent cations, or combinations thereof; and at least one copolymer, comprising:

at least one hydrophilic monomer containing acid functional groups adapted to react with the divalent cations, multivalent cations, or combinations thereof to form ionic crosslinks among polymer hydrophilic monomers present in an amount sufficient to impart a desired degree of aqueous solubility to the copolymer, the hydrophilic monomer amount ranging from about 1% to about 25% of the copolymer; and at least one hydrophobic monomer present in an amount sufficient to impart a desired degree of structural stability to the composite composition when exposed to an aqueous environment, the hydrophobic monomer amount ranging from about 75% to about 99% of the copolymer;

wherein the composite composition is adaptable for use in substantially water insoluble dental applications;

wherein the glass material further contains fluoride, and wherein the composite composition provides fluoride release;

and wherein the at least one copolymer is poly(methyl methacrylate-co-methacrylic acid) (PMMA-MAA).

29. The ionomer composite composition as defined in claim 28 wherein the ratio of PMMA to MAA is 80:20.

* * * * *